United States Patent [19]

Barger et al.

[11] 4,267,833
[45] May 19, 1981

[54] METHOD OF FLUSHING A MEDICAL FLUID

[75] Inventors: Larry N. Barger, Glendale; Kenneth R. McCord, Lakewood, both of Calif.

[73] Assignee: American Hospital Supply Corporation, Evanston, Ill.

[21] Appl. No.: 32,830

[22] Filed: Apr. 24, 1979

[51] Int. Cl.³ .............................................. A61M 5/00
[52] U.S. Cl. ................................. 128/214 F; 128/274
[58] Field of Search ............... 128/214 R, 214 F, 274, 128/227; 251/4, 117; 222/556

[56] References Cited

U.S. PATENT DOCUMENTS

| | | | |
|---|---|---|---|
| 2,706,101 | 4/1955 | Cantor | 251/4 |
| 3,675,891 | 7/1972 | Reynolds et al. | 251/117 |
| 4,106,675 | 8/1978 | Taylor | 222/556 |
| 4,109,837 | 8/1978 | Taylor | 222/556 |

FOREIGN PATENT DOCUMENTS 182656   3/1922   United Kingdom ............ 251/40 X

*Primary Examiner*—John D. Yasko
*Attorney, Agent, or Firm*—Larry N. Barger

[57] ABSTRACT

A method of flushing a medical liquid into a system that is continuously monitoring a patient's blood pressure. A parenteral liquid, such as saline, is flushed through a valve that has an elastic tube encasing a flow restrictor having a flow passage. The method includes passing the liquid through the flow passage at a predetermined rate, squeezing the tube to temporarily create an enlarged flush passage, and then releasing the tube to seal off the flush passage to force liquid through only the flow passage of the restrictor. This method of flushing can be conveniently carried out with one hand.

11 Claims, 4 Drawing Figures

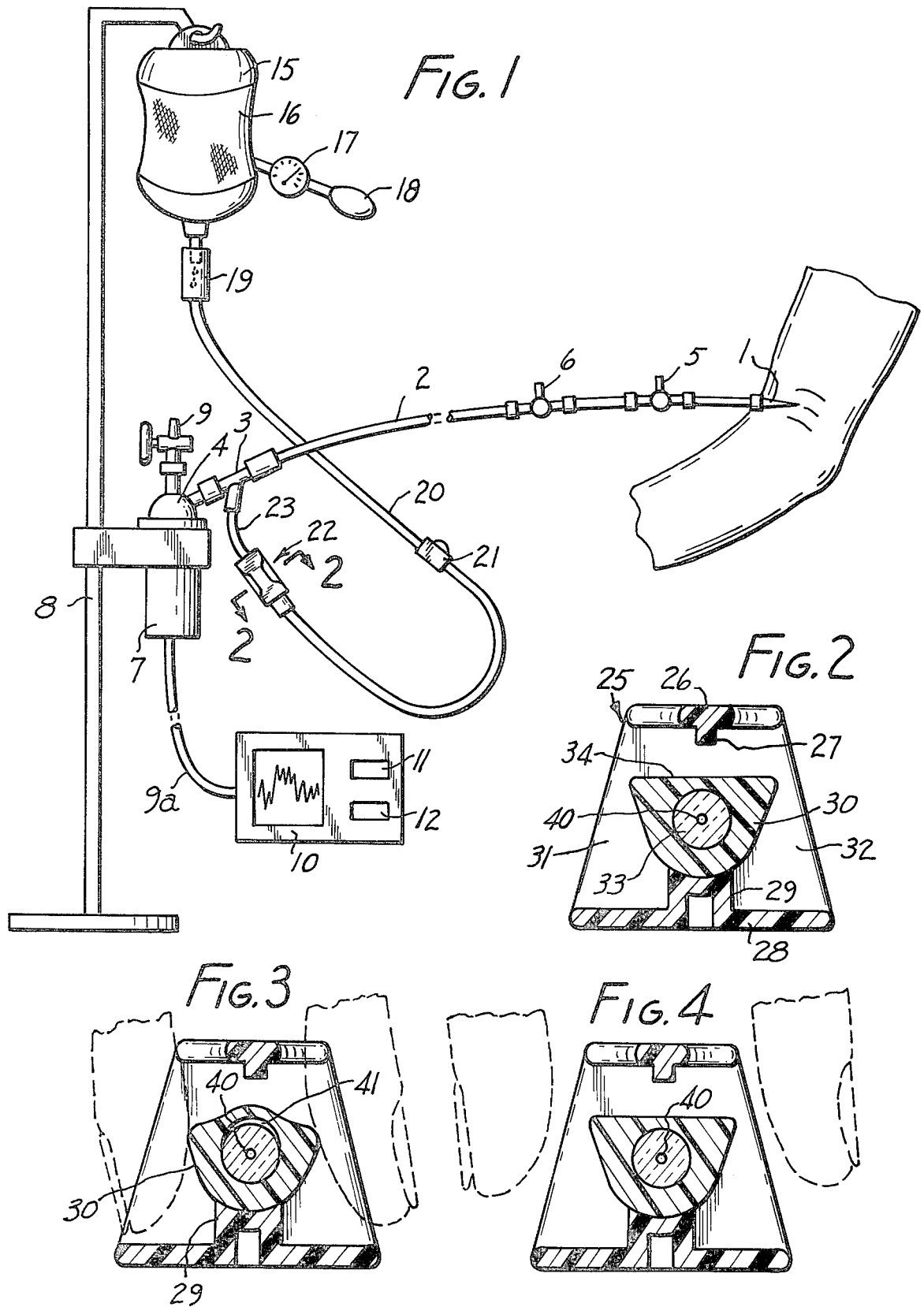

METHOD OF FLUSHING A MEDICAL FLUID

BACKGROUND

U.S. Pat. No. 3,581,733 describes a system for continuously bleeding a parenteral liquid, such as normal saline, into a patient during continuous monitoring of blood pressure. This continuous flow at a very slow rate into the patient prevents blood from entering the pressure measuring tubing where blood clots could give an erroneous reading. Periodically it becomes necessary to flush the system at a much faster rate to insure that no blood has started to coagulate around an arterial needle or catheter. Such flushing is accomplished in this patent by turning stopcock 18 so fluid flows through the flushing channel 14 rather than the restricted channel 16. Holding the stopcock in one hand and twisting the handle with another hand would be a tedious procedure, particularly when the flushing procedure had to be frequently used.

U.S. Pat. No. 3,675,891 describes a different type flushing valve in which an elongated stem is stretchingly pulled to open a valve. Enclosed is an instruction sheet for using this valve. Such stem pulling procedure has a disadvantage in that the procedure requires one hand to hold the valve and another hand to pull the stem if the valve is not firmly anchored to a supporting pole. Even if attached to a pole, a vigorous pulling of the stem could upset the whole structure.

SUMMARY OF THE INVENTION

The present invention overcomes the above problems by providing a convenient method of flushing a medical liquid that can readily be used in a one handed operation. The method includes flushing a fluid through a medical valve that has an elastic tube encasing a flow restrictor which combines with the tube to form a flow passage that can be constantly opened before, during, and after the flushing procedure. The method includes passing fluid through the flow passage at a predetermined rate, squeezing the elastic tube temporarily to form a flush passage of a substantially greater flow rate, and then releasing the tube to seal off the flush passage forcing liquid to flow only through the flow passage. The method also includes a special way of squeezing a triangularly shaped tube and also squeezing the tube through side openings in a protector housing with thumb and forefinger.

RELATED APPLICATIONS

Related co-pending co-owned applications filed on the same day as the present application are as follows:

Medical Flushing Valve and Method of Assembling Same, filed Apr. 24, 1979, Ser. No. 032,832;

System For Flushing A Medical Liquid, filed Apr. 24, 1979, Ser. No. 032,831;

Protector Housing For Squeezable Valve (Design), filed Apr. 24, 1979, Ser. No. 032,971.

THE DRAWINGS

FIG. 1 is an elevational view of a system for continuously monitoring blood pressure while slowly infusing a parenteral liquid, such as normal saline, into the patient to prevent blood coagulation in the system;

FIG. 2 is an enlarged sectional view taken along lines 2—2 of a flushing valve showing a valve as liquid is infused into the patient through the valve's flow passage;

FIG. 3 is a sectional view similar to FIG. 2 showing the valve being temporarily squeezed to create a flush passage; and FIG. 4 is a view similar to FIGS. 2 and 3 showing the valve in released condition.

DETAILED DESCRIPTION

In FIG. 1, an arterial needle or catheter 1 is joined to a connecting tube 2 which leads to a rigid T-connector 3 joined to a transducer pressure dome 4. It is understood that the term T-connector is used in its broad sense and includes angled Y-connectors. If desired, stopcocks 5 and 6 can be used with connecting tube 2 for injecting medication into the patient or extracting blood samples.

The pressure transducer dome 4 is shown rigidly attached to a transducer body 7 which is in turn attached to a supporting pole 8. The transducer dome can have an air bleed valve 9 to eliminate any air bubbles in the system prior to continuously monitoring blood pressure. The transducer which is shown attached to pole 8 has a diaphragm (not shown) inside which segregates fluid in connecting tube 2 from an electrical strain means (not shown). Thus, connecting tube 2 hydraulically couples the patient's heart to such diaphragm and pressure variations to such diaphragm are converted in the transducer to electrical impulses which are then fed through a line 9a to a monitoring instrument 10. Monitoring instrument 10 can include an oscilloscope, stylus recorder, etc. Also if desired, instrument 10 can include other readouts 11 and 12 to monitor pulse rate, etc.

To keep blood from migrating into the needle or catheter 1 and further into the connecting tube 2 where coagulation may affect the blood pressure wave, it has been proposed to continuously bleed a very small flow of parenteral liquid, such as normal saline, into the patient. This flow rate can be approximately 3 cc/hour. Such very slow flow rate does not interfere with the continuous pressure readings, but does prevent blood from backing up into the needle cannula, etc.

To supply this continuous slow flow of liquid into the patient, a pressurized parenteral liquid container 15, preferably of the collapsible bag type, has a pressure cuff 16 which is connected to a pressure gauge 17 and a pumping bulb 18. Liquid from container 15 flows through a drip chamber 19 and a feed tube 20 which can include a conventional roller clamp 21 for opening and closing the feed tube.

A flushing valve shown generally at 22 connects through a small flexible tube segment 23 to rigid connector 3. Flushing valve 22 controls the flow rate of liquid from container 15 being administered to the patient.

During normal monitoring of blood pressure, the flushing valve has the configuration shown in FIG. 2. A protector housing 25 has a top wall 26 with a narrow central section and a strengthening rib 27. The housing also includes a bottom wall 28 with a limit lug, such as cradle 29 with a concave surface, to prevent excess distortion of an elastic tube 30 of the valve during flushing. The valve has side openings 31 and 32 through which to access the elastic tube 30. Sealed within tube 30 is a glass flow restrictor 33 having a bore 40 with a diameter of from 0.001 to 0.004 inch, with 0.002 inch preferred. The elastic tube has a generally flat upper surface 34 and is generally triangular in shape. As shown in FIG. 2, all fluid is forced through a bore 40 in restrictor 30.

When it becomes necessary to fast flush the valve, a nurse or physician inserts a thumb and forefinger through the side openings in the protector housing and squeezes upper corners of the triangular sleeve to compress the sleeve along a line generally parallel to the sleeve's top surface 34. This causes an upper portion of the sleeve to substantially distort and form a flush passage 41. While this flush passage is being created, it should be noted that small bore 40 in the restrictor remains continuously open. However because of the substantial difference in the resistance to flow, essentially all of the liquid will go through the flush passage 41. After the valve has been held in the squeezed condition of FIG. 3 to complete the flushing, the valve is released as shown in FIG. 4. The elastic tube thus snaps back and seals against the restrictor, causing all of the liquid to thereafter flow through only small bore 40 in the restrictor.

During the sequence of flushing the valve, the elastic sleeve becomes substantially distorted and to protect the sleeve from overly flexing or bending to dislocate restrictor 33, cradle 29 engages the bottom area of elastic sleeve 30.

In the above description, a specific example has been used to illustrate the invention. However, it is understood by those skilled in the art that modifications can be made to this example without departing from the spirit and scope of the invention.

We claim:

1. A method of flushing a fluid through a medical valve with an elastic tube that having a noncircular outer surface, which tube encases a flow restrictor and combines with such restrictor to form a flow passage means comprising the steps of:
   (a) passing fluid through the flow passage means at a predetermined rate;
   (b) squeezing the noncircular outer surface of the tube to temporarily form a flush passage having a substantially greater flow rate;
   (c) holding the tube in squeezed condition until flushing is completed; and
   (d) releasing the tube to seal off the flush passage causing fluid to flow only through the flow passage means.

2. A method as set forth in claim 1, wherein the tube has an outer surface that is generally triangular in cross section and the squeezing force is applied at two corners of such triangle.

3. A method as set forth in claim 2, wherein the squeezing force is applied in a direction generally parallel to an external face of the tube that connects said two corners.

4. A method as set forth in claim 3, wherein the tube separates from the flow restrictor directly beneath such pinched face between said two corners.

5. A method as set forth in claim 1, wherein the valve includes a protector housing with side openings, and the method includes squeezing the tube through the housing's side openings.

6. A method as set forth in claim 5, wherein the tube is squeezed through the side openings with thumb and forefinger.

7. A method as set forth in claim 1, wherein the squeezing, holding, and releasing steps are periodically repeated during a procedure of continuously monitoring blood pressure output by a patient.

8. A method as set forth in claim 1, wherein the flow passage is from 0.001 to 0.004 inch diameter and remains continuously open during the flushing procedure.

9. A method as set forth in claim 1, wherein the method includes distorting the elastic tube while it contacts a limit lug on a protector housing of the valve.

10. A method as set forth in claim 9, wherein the elastic tube contacts a concave surface of a cradle like limit lug.

11. A method of flushing a fluid through a medical valve with an elastic tube having a noncircular outer surface that encases a flow restrictor and combines with such restrictor to form a flow passage means comprising the steps of:
   (a) passing fluid through the flow passage means at a predetermined rate;
   (b) squeezing the outer surface of the tube to temporarily form a flush passage having a substantially greater flow rate while simultaneously maintaining the flow passage means in open condition; and
   (c) releasing the tube to seal off the flush passage causing liquid to flow only through the flow passage means.

* * * * *